United States Patent
Noh et al.

(10) Patent No.: US 10,045,700 B2
(45) Date of Patent: Aug. 14, 2018

(54) BLOOD PRESSURE ESTIMATING APPARATUS AND METHOD

(71) Applicant: SAMSUNG ELECTRONICS CO., LTD., Suwon-si (KR)

(72) Inventors: Seungwoo Noh, Seongnam-si (KR); Taesung Jung, Seoul (KR); Younho Kim, Hwaseong-si (KR); Sangyun Park, Hwaseong-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 220 days.

(21) Appl. No.: 15/007,625

(22) Filed: Jan. 27, 2016

(65) Prior Publication Data

US 2017/0042433 A1 Feb. 16, 2017

(30) Foreign Application Priority Data

Aug. 11, 2015 (KR) ........................ 10-2015-0113258

(51) Int. Cl.
*A61B 5/022* (2006.01)
*A61B 5/021* (2006.01)
(Continued)

(52) U.S. Cl.
CPC ...... *A61B 5/02108* (2013.01); *A61B 5/02225* (2013.01); *A61B 5/02416* (2013.01); *A61B 5/0402* (2013.01); *A61B 5/1102* (2013.01); *A61B 5/1118* (2013.01); *A61B 5/14542* (2013.01); *A61B 5/7278* (2013.01); *A61B 5/02055* (2013.01); *A61B 5/14551* (2013.01); *A61B 2560/0223* (2013.01)

(58) Field of Classification Search
CPC ............ A61B 5/02108; A61B 5/02225; A61B 5/02416; A61B 5/0402; A61B 5/1102; A61B 5/1118; A61B 5/14542; A61B 5/7278; A61B 5/02055; A61B 5/14551; A61B 2560/0223
USPC ....... 600/485, 486, 488, 500–503, 481, 483, 600/484
See application file for complete search history.

(56) References Cited

U.S. PATENT DOCUMENTS 6,582,374 B2 6/2003 Yokozeki
7,641,614 B2 * 1/2010 Asada ............... A61B 5/02225
600/485
(Continued)

FOREIGN PATENT DOCUMENTS

JP  2000-126142 A  5/2000
JP  2001-299707 A  10/2001
(Continued)

OTHER PUBLICATIONS

Extended European Search Report dated Jan. 18, 2017 in corresponding European Application No. 16171607.1 (7 pages in English).

*Primary Examiner* — Navin Natnithithadha
(74) *Attorney, Agent, or Firm* — NSIP Law (57) ABSTRACT

A blood pressure estimating method includes measuring a biosignal including pulse wave information of a user, determining a calibration method for a blood pressure estimation model, calibrating the blood pressure estimation model using the determined calibration method, and estimating a blood pressure of the user from the biosignal using the calibrated blood pressure estimation model.

19 Claims, 7 Drawing Sheets

(51) Int. Cl.
*A61B 5/024* (2006.01)
*A61B 5/0402* (2006.01)
*A61B 5/0205* (2006.01)
*A61B 5/1455* (2006.01)
*A61B 5/11* (2006.01)
*A61B 5/145* (2006.01)
*A61B 5/00* (2006.01)

(56) References Cited

U.S. PATENT DOCUMENTS

| | | |
|---|---|---|
| 8,313,439 B2 | 11/2012 | McCombie et al. |
| 8,672,854 B2 * | 3/2014 | McCombie .......... A61B 5/0002 |
| | | 600/485 |
| 8,814,800 B2 * | 8/2014 | Fortin .................. A61B 5/0059 |
| | | 600/485 |
| 8,825,428 B2 * | 9/2014 | Addison ............. A61B 5/02125 |
| | | 702/98 |
| 8,870,782 B2 * | 10/2014 | Futatsuyama ...... A61B 5/02125 |
| | | 600/485 |
| 8,920,328 B2 * | 12/2014 | Hirabara ................ A61B 5/022 |
| | | 600/485 |
| 2010/0081944 A1 * | 4/2010 | Baker, Jr. ............... A61B 5/021 |
| | | 600/485 |
| 2010/0081945 A1 * | 4/2010 | Sethi .................. A61B 5/02007 |
| | | 600/485 |
| 2010/0081946 A1 | 4/2010 | Garudadri et al. |
| 2010/0241011 A1 | 9/2010 | McCombie et al. |
| 2010/0312115 A1 * | 12/2010 | Dentinger .......... A61B 5/02116 |
| | | 600/450 |
| 2012/0136261 A1 | 5/2012 | Sethi et al. |
| 2013/0253341 A1 * | 9/2013 | Sethi ...................... A61B 5/021 |
| | | 600/485 |

FOREIGN PATENT DOCUMENTS

| | | |
|---|---|---|
| JP | 3496820 B2 | 2/2004 |
| JP | 3631639 B2 | 3/2005 |
| JP | 2006-340896 A | 12/2006 |
| JP | 3921775 B2 | 5/2007 |
| JP | 4120083 B2 | 7/2008 |
| JP | 4713245 B2 | 6/2011 |
| JP | 4754915 B2 | 8/2011 |
| JP | 4795731 B2 | 10/2011 |
| JP | 4855721 B2 | 1/2012 |
| JP | 4971041 B2 | 7/2012 |
| JP | 5218139 B2 | 6/2013 |
| JP | 2013-132407 A | 7/2013 |
| JP | 2014-105 A | 1/2014 |
| JP | 5600728 B2 | 10/2014 |
| JP | 2015-58126 A | 3/2015 |

* cited by examiner

BLOOD PRESSURE ESTIMATING APPARATUS AND METHOD

CROSS-REFERENCE TO RELATED APPLICATION(S)

This application claims the benefit under 35 USC 119(a) of Korean Patent Application No. 10-2015-0113258 filed on Aug. 11, 2015, in the Korean Intellectual Property Office, the entire disclosure of which is incorporated herein by reference for all purposes.

BACKGROUND

1. Field

The following description relates to technology for estimating a blood pressure based on a biosignal.

2. Description of Related Art

Among numerous sets of bioinformation, blood pressure information is used as an important factor in diagnosing and treating diseases. Currently, a most widely used automated electronic sphygmomanometer, or electronic blood pressure meter, applies an oscillometric method. The oscillometric method is used to measure a blood pressure based on an oscillation generated when increasing and decreasing a pressure of an artery using a cuff, and estimate, as a mean blood pressure, a cuff pressure measured when a pulse from a heartbeat has a maximum amplitude.

A blood pressure changes over time, and thus measuring a blood pressure one time may be insufficient to determine a state of a user. Thus, continuously measuring a blood pressure may be needed. Recently, research and development s being conducted on technology for continuously measuring a blood pressure using a pulse transit time (PTT) or pulse wave analysis (PWA) method, in lieu of a one-time measuring method such as a method of measuring a blood pressure by wrapping a cuff around an arm.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

In one general aspect, a blood pressure estimating method includes measuring a biosignal including pulse wave information of a user; determining a calibration method for a blood pressure estimation model; calibrating the blood pressure estimation model using the determined calibration method; and estimating a blood pressure of the user from the biosignal using the calibrated blood pressure estimation model.

The determining of the calibration method may include determining the calibration method for the blood pressure estimation model based on either one or both of a signal quality of the biosignal and an elapsed time since a previous calibration of the blood pressure estimation model was performed.

The determining of the calibration method may include determining the calibration method for the blood pressure estimation model based on any one or any combination of any two or more of movement information of the user, external temperature information, and body temperature information of the user.

The determined calibration method may be selected from a first calibration method of calibrating the blood pressure estimation model based on a blood pressure value measured using a cuff, and a second calibration method of measuring another biosignal and calibrating the blood pressure estimation model based on the other measured biosignal.

The determining of the calibration method may include determining that the second calibration method is to be performed between points in time at which the first calibration method is performed.

The biosignal may be a photoplethysmogram (PPG) signal; and the other biosignal may be an electrocardiogram (ECG) signal or a biosignal including blood oxygen saturation ($SpO_2$) information.

The method may further include determining whether to calibrate the blood pressure estimation model; and the determining of the calibration method may include determining the calibration method for the blood pressure estimation model in response to a result of the determining of whether to calibrate the blood pressure estimation model being to calibrate the blood pressure estimation model.

The determining of whether to calibrate the blood pressure estimation model may include determining whether to calibrate the blood pressure estimation model based on either one or both of a signal quality of the biosignal and an elapsed time since a previous calibration of the blood pressure estimation model was performed.

The determining of whether to calibrate the blood pressure estimation model may include determining whether to calibrate the blood pressure estimation model based on any one or any combination of any two or more of movement information of the user, external temperature information, and body temperature information of the user.

The measuring of the biosignal may include measuring biosignals of a same type, and selecting a reference biosignal from the biosignals based on signal qualities of the biosignals; and the estimating of the blood pressure of the user may include estimating the blood pressure of the user from the reference biosignal using the calibrated blood pressure estimation model.

In another general aspect, a non-transitory computer-readable storage medium stores instructions to cause computing hardware to perform the method described above.

In another general aspect, a blood pressure estimating apparatus includes a first sensor configured to measure a biosignal including pulse wave information of a user; a calibration controller configured to determine a calibration time at which a calibration is to be performed on a blood pressure estimation model and a calibration method for the blood pressure estimation model; a calibrator configured to calibrate the blood pressure estimation model at the determined calibration time using the determined calibration method; and a blood pressure estimator configured to estimate a blood pressure of the user from the biosignal using the calibrated blood pressure estimation model.

The calibration controller may be further configured to determine the calibration time and the calibration method based on either one or both of a signal quality of the biosignal and an elapsed time since a previous calibration of the blood pressure estimation model was performed.

The calibration controller may be further configured to determine the calibration time and the calibration method based on any one or any combination of any two or more of movement information of the user, external temperature information, and body temperature information of the user.

The calibration controller may be further configured to control an operation of the first sensor.

The calibration controller may be further configured to select the calibration method for the blood pressure estimation model from a first calibration method of calibrating the blood pressure estimation model based on a blood pressure value measured using a cuff, and a second calibration method of calibrating the blood pressure estimation model based on another biosignal.

The apparatus may further include any one or any combination of any two or more of a second sensor configured to measure another biosignal, a third sensor configured to measure a movement of the user, and a fourth sensor configured to measure either one or both of a body temperature of the user and an external temperature; and the calibrator may be further configured to calibrate the blood pressure estimation model based on any one or any combination of any two or more of the other biosignal sensed by the second sensor, the movement information measured by the third sensor, and the body temperature and the external temperature sensed by the fourth sensor.

The apparatus may further include a signal selector configured to receive the biosignal sensed by the first sensor, the other biosignal sensed by the second sensor, movement information measured by the third sensor, and the body temperature and the external temperature sensed by the fourth sensor, output, to the blood pressure estimator, the biosignal sensed by the first sensor, and output, to the calibrator, any one or any combination of any two or more of the other biosignal sensed by the second sensor, the movement information measured by the third sensor, and the body temperature and the external temperature sensed by the fourth sensor.

In another general aspect, a blood pressure estimating apparatus includes a first sensor configured to sense a first biosignal of a user; a blood pressure estimator configured to estimate a blood pressure of the user from the first biosignal using a blood pressure estimation model; a calibrator configured to calibrate the blood pressure estimation model using a plurality of calibration methods; and a calibration controller configured to select one of the calibration methods, and control the calibrator to calibrate the blood pressure estimation model using the selected calibration method.

The apparatus may further include a second sensor configured to sense a second biosignal of the user; and the plurality of calibration methods may include a first calibration method in which the calibrator calibrates the blood pressure estimation model based on a blood pressure of the user measured using a cuff; and a second calibration method in which the calibrator calibrates the blood pressure estimation model based on the first biosignal and the second biosignal.

The first biosignal may be a photoplethysmogram (PPG) signal; the second biosignal may be a electrocardiogram (ECG) signal; and the calibrator may be further configured to calculate a blood pressure based on the PPG signal and the ECG signal and calibrate the blood pressure estimation model based on the calculated blood pressure in the second calibration method.

The calibration controller may be further configured to alternately select the first calibration method and the second calibration method.

The calibration controller may be further configured to determine a signal quality of the first biosignal, select the first calibration method in response to either the signal quality of the first biosignal being less than or equal to a predetermined threshold or a predetermined amount of time elapsing since a last calibration of the blood pressure estimation model was performed, and select the second calibration method in response to the first calibration method not being selected.

The apparatus may further include at least one additional first sensor configured to sense a first biosignal of the user so that the apparatus includes a plurality of first sensors configured to sense a plurality of first biosignals of the user at a plurality of different sensing locations on the user; and a signal selector configured determine respective signal qualities of the first biosignals, select one of the first biosignals having a highest signal quality, and output the selected first biosignal to the blood pressure estimator.

Other features and aspects will be apparent from the following detailed description, the drawings, and the claims.

BRIEF DESCRIPTION OF THE DRAWINGS

FIGS. 2 through 3B illustrate an example of a calibration to be performed over time.

FIG. 3 is a flowchart illustrating an example of a blood pressure estimating method.

Throughout the drawings and the detailed description, the same reference numerals refer to the same elements. The drawings may not be to scale, and the relative size, proportions, and depiction of elements in the drawings may be exaggerated for clarity, illustration, and convenience.

DETAILED DESCRIPTION

The following detailed description is provided to assist the reader in gaining a comprehensive understanding of the methods, apparatuses, and/or systems described herein. However, various changes, modifications, and equivalents of the methods, apparatuses, and/or systems described herein will be apparent to one of ordinary skill in the art. The sequences of operations described herein are merely examples, and are not limited to those set forth herein, but may be changed as will be apparent to one of ordinary skill in the art, with the exception of operations necessarily occurring in a certain order. Also, descriptions of functions and constructions that are well known to one of ordinary skill in the art may be omitted for increased clarity and conciseness.

The features described herein may be embodied in different forms, and are not to be construed as being limited to the examples described herein. Rather, the examples described herein have been provided so that this disclosure will be thorough and complete, and will convey the full scope of the disclosure to one of ordinary skill in the art.

Terms such as first, second, A, B, (a), and (b) may be used herein to describe components. Each of these terminologies is not used to define an essence, order, or sequence of a corresponding component, but is used merely to distinguish the corresponding component from other component(s). In addition, the terminology used herein is for the purpose of describing particular examples only, and is not intended to limit the disclosure. As used herein, the singular forms "a," "a," and "the" are intended to include the plural forms as well, unless the context clearly indicates otherwise. As used herein, the terms "include," "comprise," and "have" specify the presence of stated features, numbers, operations, elements, components, or combinations thereof, but do not preclude the presence or addition of one or more other features, numbers, operations, elements, components, or combinations thereof.

Examples described hereinafter relate to a method used to increase accuracy in estimating a blood pressure by calibrating a blood pressure estimation model when continuously estimating a blood pressure from a biosignal including pulse wave information using the blood pressure estimation model. A blood pressure is a pressure against a wall of a blood vessel while blood pumped from the heart is flowing in the blood vessel. A pulse wave is a wave formed when a pulse propagates to a peripheral arteriole. A pulse is a repetition of expansion and relaxation of an artery occurring due to a blood flow pushing blood along the artery at each heartbeat. Each time when the heart contracts, blood is supplied to the entire body from the heart through the aorta, and a change in a pressure of a main artery occurs. Such a change in the pressure propagates to a peripheral arteriole of a hand and a foot, and is reflected in a waveform, that is, a pulse wave.

Figure 1:
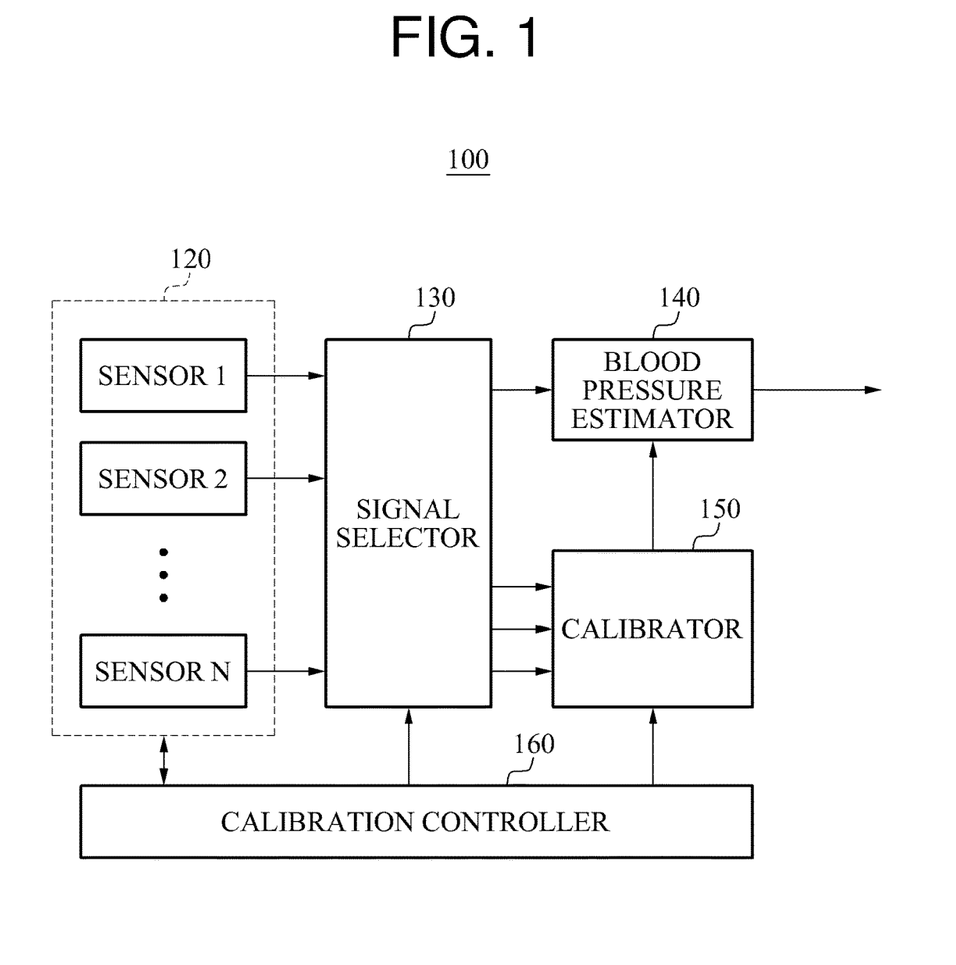
FIG. 1 is a diagram illustrating an example of a blood pressure estimating apparatus.

FIG. 1 is a diagram illustrating an example of a blood pressure estimating apparatus 100. The blood pressure estimating apparatus 100 measures a biosignal from a body of a user, and estimates a blood pressure of the user from the biosignal using a blood pressure estimation model. In one example, the blood pressure estimating apparatus 100 is provided in a form of a wearable device that may be worn by the user. The blood pressure estimating apparatus 100 may continuously estimate a blood pressure of the user while the user is wearing the wearable device.

The blood pressure estimating apparatus 100 calibrates the blood pressure estimation model to compensate for a decrease in accuracy of the blood pressure estimation model due to a lapse of time or a change in an environment in which measurement is performed. The blood pressure estimating apparatus 100 selects a calibration method most suitable for a current situation from various calibration methods, and calibrates the blood pressure estimation model based on the selected calibration method. Hereinafter, components of the blood pressure estimating apparatus 100 will be described in detail.

Referring to FIG. 1, the blood pressure estimating apparatus 100 includes a sensor unit 120, a signal selector 130, a calibrator 150, a blood pressure estimator 140, and a calibration controller 160. The signal selector 130, the calibrator 150, the blood pressure estimator 140, and the calibration controller 160 may be implemented by at least one processor.

The sensor unit 120 includes various sensors. For example, the sensor unit 120 includes a sensor configured to directly or indirectly measure pulse wave information of a user by sensing a biosignal of the user, and a sensor used to obtain an auxiliary signal used to calibrate a blood pressure estimation model.

The sensor configured to measure the pulse wave information is a sensor configured to measure, for example, a photoplethysmogram (PPG), an electrocardiogram (ECG), a blood oxygen saturation ($SpO_2$) level, and a ballistocardiogram (BCG), or a sensor configured to measure a change in a blood flow using an ultrasonic Doppler or a laser Doppler method.

The sensor used to obtain the auxiliary signal is, for example, an inertial sensor such as an acceleration sensor, a gyro sensor, a shock sensor, or a tilt sensor, a temperature sensor, or a global positioning system (GPS) sensor.

However, the sensors are not limited to the sensors described in the foregoing paragraphs, and the sensor unit 120 may include various sensors in addition to the sensors described in the foregoing paragraphs.

The signal selector 130 selects, from sensed signals received from the sensor unit 120, a main signal as a biosignal used to estimate a blood pressure and outputs the selected main signal to the blood pressure estimator 140. In addition, the signal selector 130 selects, from the sensed signals, a sensed signal as the auxiliary signal to be used to calibrate the blood pressure estimation model, and outputs the selected auxiliary signal to the calibrator 150. In one example, the signal selector selects, from the sensed signals, a plurality of auxiliary signals to be used to calibrate the blood pressure estimation model in a plurality of different calibrations depending on a situation.

The blood pressure estimator 140 estimates a blood pressure of the user based on the main signal received from the signal selector 130. For example, when the blood pressure estimator 140 receives a PPG signal from the signal selector 130, the blood pressure estimator 140 analyzes the PPG signal using a pulse wave analysis (PWA) method, and calculates a blood pressure value corresponding to the PPG signal using the blood pressure estimation model.

For example, the blood pressure estimator 140 may obtain an accelerated plethysmographic waveform by taking the second derivative of a PPG signal including pulse wave information, and analyze a peak characteristic from the accelerated plethysmographic waveform. Through the analyzing of the peak characteristic, an aging degree of a blood vessel or an age of the blood vessel may be calculated. A correlation between the peak characteristic of the accelerated plethysmographic waveform and the blood pressure value is predefined in the blood pressure estimation model, and the blood pressure estimator 140 obtains a blood pressure value corresponding to a peak characteristic from the blood pressure estimation model by inputting, to the blood pressure estimation model, the peak characteristic, for example, each peak value and a time interval between peak values.

In one example, the sensor unit 120 includes a plurality of sensors configured to sense signals of a same type. For example, the sensor unit 120 includes a plurality of sensors configured to measure a PPG signal at different sensing locations. The signal selector 130 selects a reference PPG signal to be used to estimate a blood pressure from the PPG signals output from the plurality of sensors, and outputs the selected reference PPG signal to the blood pressure estimator 140. The signal selector 130 determines the reference PPG signal to be a PPG signal having a highest signal quality, for example, a highest signal-to-noise ratio (SNR). The blood pressure estimator 140 estimates a blood pressure of the user from the reference PPG signal received from the signal selector 130.

The calibrator 150 calibrates the blood pressure estimation model based on at least one auxiliary signal received from the signal selector 130. A calibration time at which a calibration is to be performed on the blood pressure estimation model and a calibration method for the blood pressure estimation model are determined by the calibration controller 160. The calibrator 150 calibrates the blood pressure estimation model at the determined calibration time and using the determined calibration method. Through the calibration, parameters to be applied to the blood pressure estimation model are updated, and an accuracy of the blood pressure estimation model in estimating a blood pressure is increased. When the calibration is completed, the blood pressure estimator 140 estimates the blood pressure of the user from the main signal using the calibrated blood pressure estimation model.

The calibration controller 160 controls a calibration process. The calibration controller 160 determines whether a calibration is currently needed. In response to a determination that the calibration is needed, the calibration controller 160 determines a calibration method most suitable for a current situation. The calibration controller 160 controls an operation of each sensor included in the sensor unit 120 based on the determined calibration time and the calibration method. For example, the calibration controller 160 controls activation and deactivation of each sensor and power to be supplied to each sensor. Thus, through such a calibration process, a power consumption efficiency increases.

In one example, the calibration controller 160 calculates a signal quality of a biosignal used to estimate a blood pressure, and determines that the calibration is to be performed in response to the signal quality being less than or equal to a predetermined threshold.

In another example, the calibration controller 160 determines that the calibration is to be performed based on a preset time pattern. For example, the calibration controller 160 determines the calibration to be performed at predetermined intervals.

The calibration controller 160 determines an accuracy of the estimated blood pressure value calculated from the blood pressure estimator 140, and determines a cause of a low level of accuracy when the accuracy is determined to be low. For example, the calibration controller 160 determines a situation in which a level of accuracy is lowered by detecting a waveform change in a biosignal to be measured, a change in a signal to be sensed by the inertial sensor, and a change in an external temperature or a body temperature. The calibration controller 160 determines the calibration method for the blood pressure estimation model based on the determined situation.

In one example, the calibration controller 160 detects a change in a situation based on the auxiliary signal sensed from the sensor unit 120, and determines that the calibration is to be performed when the level of accuracy in estimating a blood pressure is determined to be lowered due to the change in the situation. For example, the calibration controller 160 determines that the calibration is to be performed when a change in the external temperature is greater than or equal to a predetermined threshold or a movement of the user is detected based on the auxiliary signal. The calibration controller 160 may more accurately determine a point in time at which the calibration is needed for the blood pressure estimation model by simultaneously analyzing a change in a biosignal and a change in an external environment.

In addition, the calibration controller 160 determines an optimal calibration method suitable for a current situation. In one example, the calibration controller 160 determines the current situation using body temperature information of the user and external temperature information that are sensed through the temperature sensor, movement information of the user sensed through the inertial sensor, location information of the user sensed through the GPS sensor, and determines the calibration method based on the current situation.

For example, when a change in an external temperature is detected to be greater than or equal to the predetermined threshold, the calibration controller 160 determines that the calibration is to be performed to compensate for an offset in the blood pressure estimation model due to the temperature change. In another example, when a movement of the user is detected, the calibration controller 160 predicts a degree of contraction and dilatation of a diameter of a blood vessel, and determines that the calibration is to be performed to compensate for an offset in the blood pressure estimation model due a change in the diameter of the blood vessel.

In one example, the calibration method includes a first calibration method to calibrate the blood pressure estimation model based on a blood pressure value measured using a cuff, and a second calibration method to calibrate the blood pressure estimation model based on another biosignal. For example, the second calibration method additionally measures an ECG signal in addition to the PPG signal used to estimate the blood pressure, calculates a pulse transit time (PTT) based on the PPG signal and the ECG signal, and calibrates the blood pressure estimation model using the PTT.

The PTT indicates an amount of time during which blood arrives at a distal portion of the body such as a fingertip or a toe after starting from a heart, and is determined by calculating a time difference between an R-peak point of the ECG signal and a starting point of the PPG signal. A correlation between the PTT and the blood pressure is predefined, and the calibrator 150 calculates the PTT based on the ECG signal and the PPG signal measured by the sensor unit 120, and calculates a blood pressure value corresponding to the PTT using the correlation. The calibrator 150 calibrates the blood pressure estimation model by training the blood pressure estimation model so that the calculated blood pressure value is output from the blood pressure estimation model.

When a predetermined amount of time has elapsed after the calibration performed on the blood pressure estimation model using the first calibration method or a signal quality of the PPG signal decreases to be less than or equal to a predetermined threshold, the calibration controller 160 measures the ECG signal from the user in addition to the PPG signal and determines that the calibration is to be performed on the blood pressure estimation model based on the PPG signal and the ECG signal using the second calibration method.

As described in the foregoing, the blood pressure estimating apparatus 100 maintains a desired level of accuracy or higher in estimating a blood pressure by calibrating a blood pressure estimation model based on a calibration method suitable for a situation in which the calibration is needed. In addition, the blood pressure estimating apparatus 100 performs different calibration methods based on a situation, and thus improves a user convenience by reducing a frequency of calibrations performed using a cuff.

Figure 2:
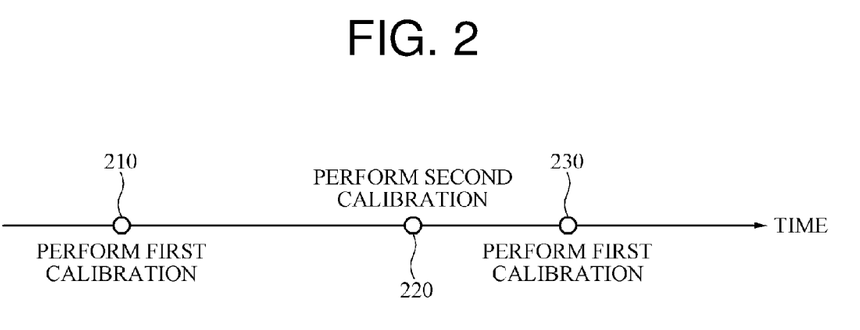
Figure 3A:
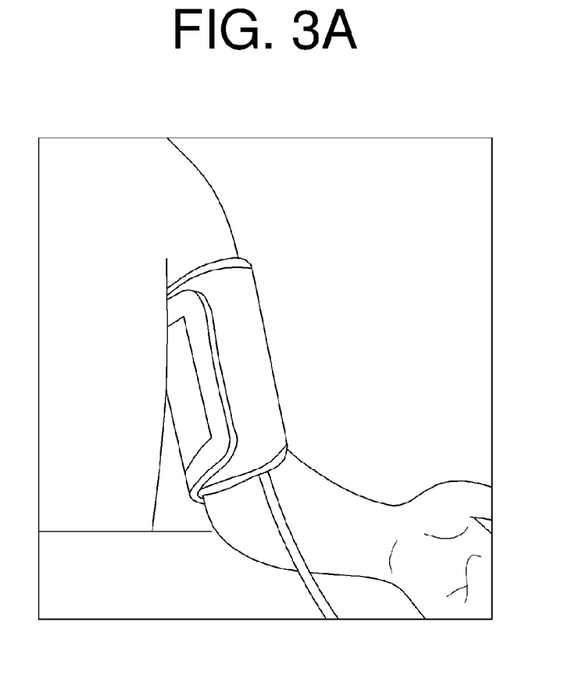
Figure 3B:
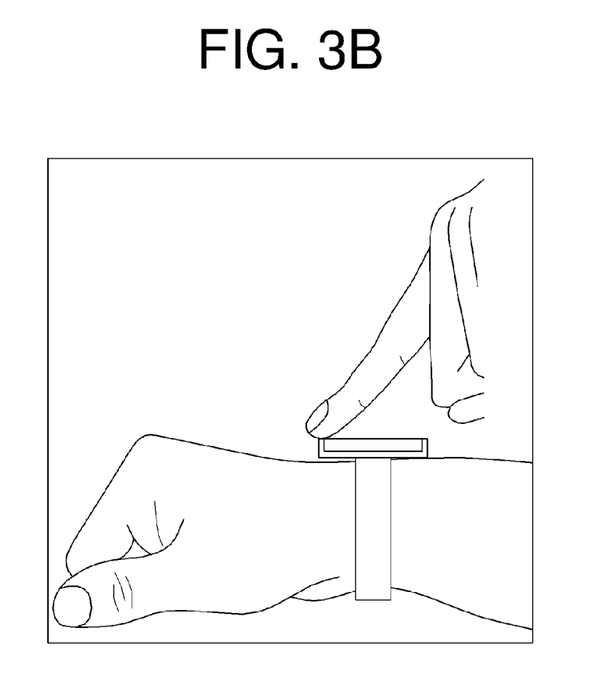

FIGS. 2 through 3B illustrate an example of a calibration to be performed over time.

Referring to FIG. 2, a blood pressure estimating apparatus performs a first calibration at a point 210 and a point 230 in time. For example, when a user measures a blood pressure value while a cuff is wound around an upper arm of the user as illustrated in FIG. 3A and inputs the measured blood pressure value to the blood pressure estimating apparatus, the first calibration is a calibration method of calibrating a blood pressure estimation model by the blood pressure estimating apparatus based on the input blood pressure value. The first calibration includes updating parameters of the blood pressure estimation model so that the blood pressure value measured using the cuff is output from the blood pressure estimation model. When the blood pressure estimating apparatus determines that the first calibration is needed, the blood pressure estimating apparatus outputs a message requesting the user to measure the blood pressure value using the cuff and input the measured blood pressure value.

A point in time at which the blood pressure estimating apparatus requests the first calibration may be determined based on a signal quality of a PPG signal sensed by a sensor, a lapse of time, or a change in a situation, for example, a change in an external temperature and a detected movement of the user.

The blood pressure estimating apparatus performs a second calibration, which is a simpler calibration than the first calibration, at a point 220 between the point 210 and the point 230 in time. For example, when a predetermined amount of time has elapsed after the point 210 or a situation occurs at the point 220, for example, when a change in an external temperature is greater than or equal to a predetermined threshold or when a movement of the user is detected, the blood pressure estimating apparatus senses an ECG signal in addition to the PPG signal as illustrated in FIG. 3B and performs the second calibration using the PPG signal and the ECG signal. When the blood pressure estimating apparatus determines that the second calibration is needed, the blood pressure estimating apparatus outputs a message requesting the user to make contact with a sensor with both hands.

For example, the blood pressure estimating apparatus calculates a PTT based on a time difference between a PPG signal and an ECG signal, calculates a blood pressure value of a user based on the calculated PTT, and calibrates a blood pressure estimation model based on the calculated blood pressure value. For example, when the blood pressure estimation model receives the PPG signal, the blood pressure estimating apparatus adjusts the parameters of the blood pressure estimation model to output the blood pressure value calculated based on the PTT.

As described in the foregoing, a user convenience is improved by using the second calibration that is a simpler calibration method to be performed between points in time at which the first calibration using the cuff is performed, and with a reduced frequency of performing the first calibration.

Figure 4:
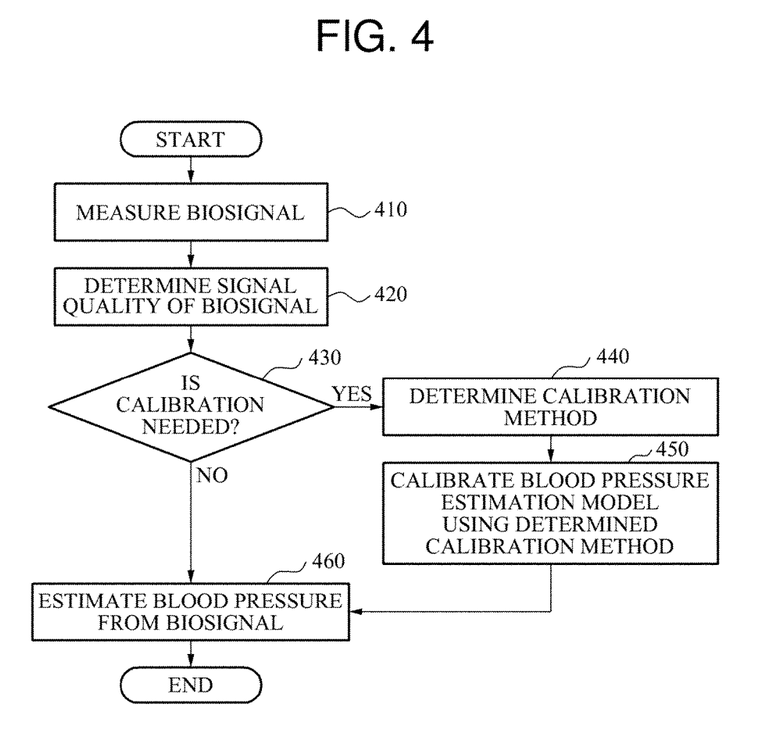

FIG. 4 is a flowchart illustrating an example of a blood pressure estimating method. The blood pressure estimating method described hereinafter may be performed by a blood pressure estimating apparatus implemented by at least one processor.

Referring to FIG. 4, in operation 410, the blood pressure estimating apparatus measures a biosignal, for example, a PPG signal, including pulse wave information of a user through a sensor. In operation 420, the blood pressure estimating apparatus determines a signal quality, for example, an SNR, of the biosignal.

In operation 430, the blood pressure estimating apparatus determines whether a calibration is needed for a blood pressure estimation model. For example, the blood pressure estimating apparatus determines whether to calibrate the blood pressure estimation model based on either one or both of the signal quality of the biosignal determined in operation 420 and an elapsed time since the previous calibration was performed. When the signal quality of the biosignal is less than or equal to a predetermined threshold or a predetermined amount of time has elapsed since the previous calibration was performed, the blood pressure estimating apparatus determines that the calibration is to be performed on the blood pressure estimation model.

In another example, the blood pressure estimating apparatus determines whether to calibrate the blood pressure estimation model based on any one or any combination of any two or more of movement information of the user, external temperature information, and body temperature information of the user. The blood pressure estimating apparatus determines whether a change in a situation that may affect a blood pressure has occurred based on this information, and determines that the calibration of the blood pressure estimation model is needed in response to a determination that the change in the situation has occurred.

In operation 460, when the blood pressure estimating apparatus determines in operation 430 that the calibration of the blood pressure estimation model is not needed, the blood pressure estimating apparatus estimates a blood pressure of the user from the biosignal using the blood pressure estimation model. For example, the blood pressure estimating apparatus analyzes a waveform of the PPG signal using a PWA method, and estimates a blood pressure value based on a result of the analyzing.

In operation 440, when the blood pressure estimating apparatus determines in operation 430 that the calibration is to be performed on the blood pressure estimation model, the blood pressure estimating apparatus determines a calibration method for the blood pressure estimation model.

In one example, the blood pressure estimating apparatus determines the calibration method based on either one or both of a signal quality of the biosignal and an elapsed time since the previous calibration was performed. The calibration method includes a first calibration method of calibrating the blood pressure estimation model based on a blood pressure value measured using a cuff, and a second calibration method of measuring another biosignal and calibrating the blood pressure estimation model based on the measured other biosignal. For example, the second calibration method includes measuring an ECG signal in addition to the PPG signal including pulse wave information, and calibrating the blood pressure estimation model using a PTT calculated based on the PPG signal and the ECG signal.

For example, when the signal quality of the biosignal is less than or equal to a predetermined threshold or when a predetermined amount of time has elapsed since the previous calibration was performed, the blood pressure estimating apparatus determines to calibrate the blood pressure estimation model using the first calibration method. When a degradation of the signal quality of the biosignal is not large or when an insignificant amount of time has elapsed since the previous calibration was performed, the blood pressure estimating apparatus determines to calibrate the blood pressure estimation model using the second calibration method.

Although the second calibration method has a relatively lower level of calibration accuracy compared to the first calibration method, the second calibration method is simpler and requires less time for the calibration compared to the first calibration method. The blood pressure estimating apparatus determines that the second calibration method is to be performed between points in time at which the first calibration method is performed to reduce a frequency of calibrations performed using the first calibration method.

In another example, the blood pressure estimating apparatus determines the calibration method based on any one or any combination of any two or more of movement information of the user, external temperature information, and body temperature information of the user measured through a sensor. For example, the blood pressure estimating apparatus determines that a change of an external temperature is greater than or equal to a threshold based on this information. In such an example, the blood pressure estimating apparatus determines to compensate for the effect of a change in a temperature on the blood pressure estimation model.

In operation 450, the blood pressure estimating apparatus calibrates the blood pressure estimation model using the calibration method determined in operation 440. In operation 460, the blood pressure estimating apparatus estimates a blood pressure of the user from the biosignal using the calibrated blood pressure estimation model. For example, the blood pressure estimating apparatus analyzes a waveform of the PPG signal using a PWA method, and estimates the blood pressure of the user based on a result of the analyzing using the calibrated blood pressure estimation model.

Figure 5:
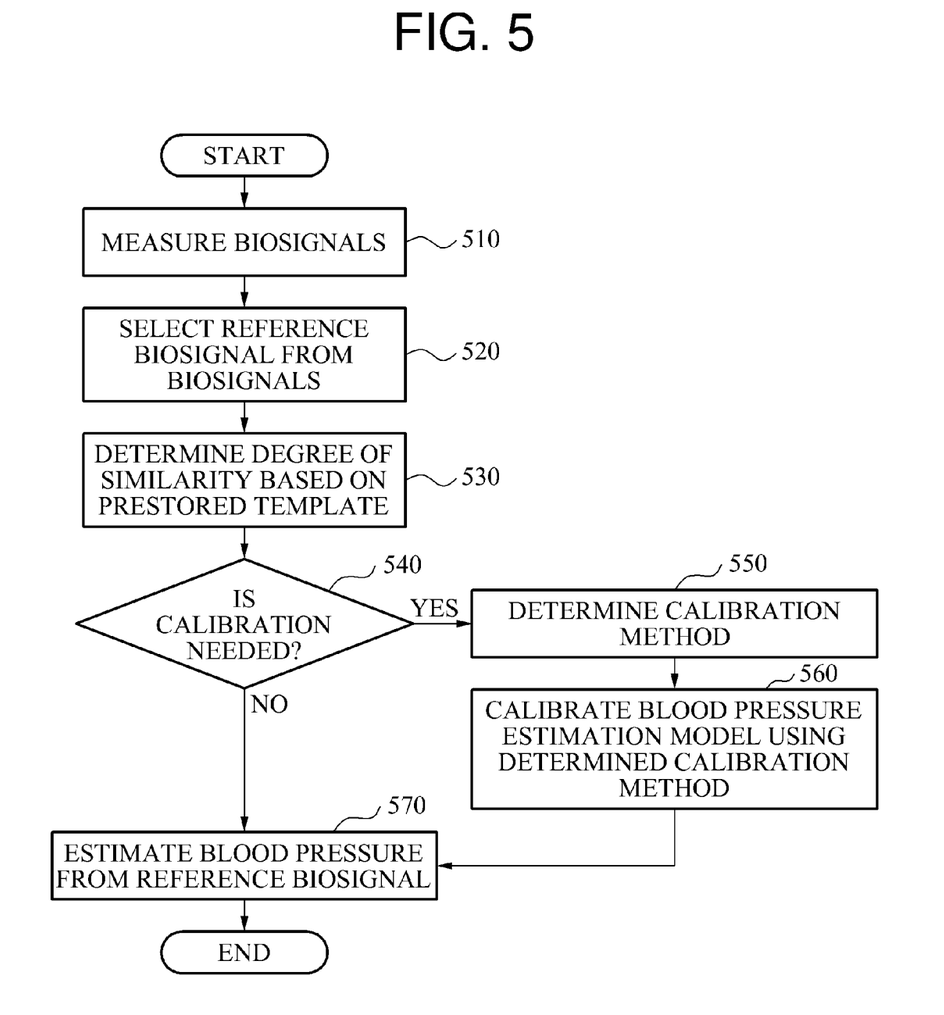
FIG. 5 is a flowchart illustrating another example of a blood pressure estimating method.

FIG. 5 is a flowchart illustrating another example of a blood pressure estimating method. The blood pressure estimating method described hereinafter may be performed by a blood pressure estimating apparatus implemented by at least one processor.

Referring to FIG. 5, in operation 510, the blood pressure estimating apparatus measures a plurality of biosignals of a same type, for example, PPG signals, using a plurality of sensors at different sending locations. In operation 520, the blood pressure estimating apparatus selects a reference biosignal from the biosignals. For example, the blood pressure estimating apparatus determines signal qualities of the biosignals and selects, as the reference biosignal, a biosignal having an optimal signal quality, for example, a highest signal quality, such as a highest SNR.

In operation 530, the blood pressure estimating apparatus determines a degree of similarity, or correlation, between the reference biosignal and a biosignal prestored in a template. For example, in a normal state, such as a state in which a user rests in a motionless state, information about a waveform of a measured PPG signal in the normal state and information about a correlation between the PPG signal and other sensed signals in the normal state are prestored in the template. For example, the blood pressure estimating apparatus calculates a degree of similarity between two signals by comparing a waveform of a currently measured PPG signal and the waveform of a PPG signal in the normal state stored in the template.

In operation 540, the blood pressure estimating apparatus determines whether a calibration of a blood pressure estimation model is needed. For example, when the degree of similarity calculated in operation 530 is less than or equal to a predetermined threshold, the blood pressure estimating model determines that the calibration of the blood pressure estimation model is needed. In another example, the blood pressure estimating apparatus more accurately determines a point in time at which the calibration needs to be performed by determining a contraction and relaxation state of a blood vessel based on a change in a temperature and a degree of activity performed by the user using any one or any combination of any two or more of an external temperature, a body temperature, and a movement of the user measured as environment variables.

In operation 570, when the blood pressure estimating apparatus determines that the calibration is not needed, the blood pressure estimating apparatus estimates a blood pressure of the user from the reference biosignal using the blood pressure estimation model. For example, the blood pressure estimating apparatus analyzes a waveform of the reference biosignal using a PWA method, and estimates a blood pressure value based on a result of the analyzing.

In operation 550, when the blood pressure estimating apparatus determines in operation 540 that the calibration is needed, the blood pressure estimating apparatus determines a calibration method for the blood pressure estimation model. In one example, the blood pressure estimating apparatus determines the calibration model to be any one of the calibration methods described in connection with operation 440 in FIG. 4 and a calibration method based on $SpO_2$ information. In operation 560, the blood pressure estimating apparatus calibrates the blood pressure estimation model using the determined calibration method.

$SpO_2$ is defined as a ratio of a concentration of hemoglobin containing oxygen ($HbO_2$) in the blood to a total concentration of hemoglobin in the blood, and is calculated based on the Beer-Lambert law. The blood pressure estimating apparatus includes a sensor configured to measure by transmitting light having different wavelengths through a tissue of the user, such as a fingertip, and measuring absorptions of the two wavelengths in the tissue, calculating a ratio of the absorptions, and calculating $SpO_2$ based on the calculated ratio. The $SpO_2$ reflects therein information about a diameter of a blood vessel. In one example, the blood pressure estimating apparatus calibrates the blood pressure estimation model by predicting a current blood vessel diameter based on the calculated $SpO_2$, and compensating for the blood vessel diameter predicted from the blood pressure estimation model.

In operation 570, the blood pressure estimating apparatus estimates a blood pressure of the user from the reference biosignal using the calibrated blood pressure estimation model. For example, the blood pressure estimating apparatus analyzes a waveform of the reference biosignal using a PWA method, and estimates the blood pressure of the user based on a result of the analyzing using the calibrated blood pressure estimation model.

Figure 6:
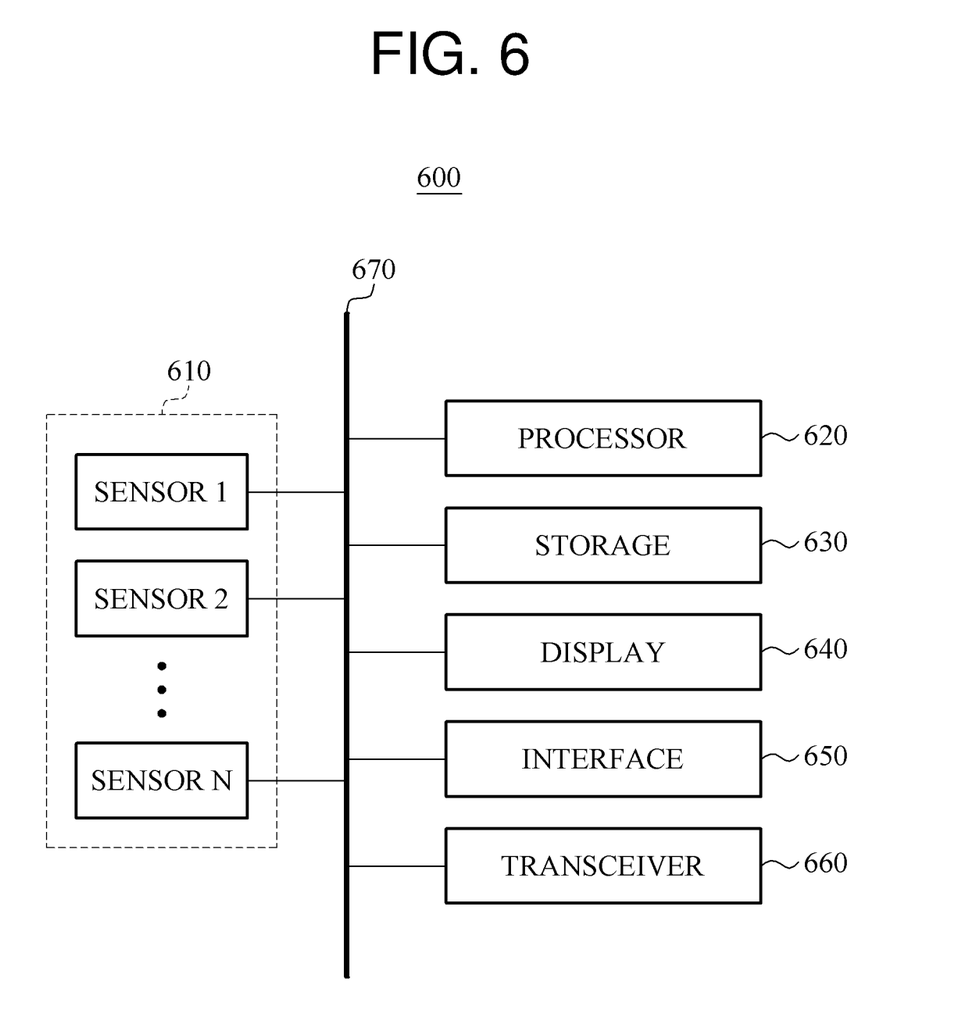
FIG. 6 is a diagram illustrating another example of a blood pressure estimating apparatus.

FIG. 6 is a diagram illustrating another example of a blood pressure estimating apparatus 600.

Referring to FIG. 6, the blood pressure estimating apparatus 600 includes a sensor unit 610, a processor 620, a storage 630, a display 640, an interface 650, and a transceiver 660. The sensor unit 610, the processor 620, the storage 630, the display 640, the interface 650, and the transceiver 660 communicate with one another through a bus 670.

The sensor unit 610 includes a sensor configured to measure a biosignal from a portion of the body on which measurement is performed, and a sensor configured to measure an auxiliary signal used to calibrate a blood pressure estimation model. The measured biosignal and the auxiliary signal are transmitted to the processor 620.

The processor 620 includes at least one component described with reference to FIGS. 1 through 5, or perform at least one method described with reference to FIGS. 1 through 5. For example, the processor 620 includes the signal selector 130, the calibrator 150, the blood pressure estimator 140, and the calibration controller 160 illustrated in FIG. 1. The processor 620 may be configured as an array of multiple logic gates, or may be implemented as a combination of a microprocessor and a memory in which a program to be executed by the microprocessor is stored. In addition, it will be apparent one of ordinary skill in the art to which this disclosure pertains that the processor 620 may be implemented as hardware having other forms.

The storage 630 stores results performed, processed, or obtained by the processor 620, and the processor 620 reads out information stored in the storage 630 when the information stored in the storage 630 is needed. The storage 630 may be a non-transitory computer-readable storage medium storing a memory and/or a template such as a volatile memory and a nonvolatile memory.

The blood pressure estimating apparatus 600 outputs, through the display 640, blood pressure information estimated by the processor 620 and information about the biosignal and the auxiliary signal measured by the sensor unit 610.

The blood pressure estimating apparatus 600 outputs, through the display 640, a blood pressure value estimated from the blood pressure estimation model to provide a user with a change in the blood pressure value.

The blood pressure estimating apparatus 600 receives, through the interface 650, user information including a gender, an age, a height, a weight, and other information of the user, and estimates a blood pressure of the user based on the received user information.

When the blood pressure of the user estimated based on the biosignal is determined to deviate from a normal range, the blood pressure estimating apparatus 600 informs the user of a risk associated with the abnormal blood pressure. For example, when the blood pressure estimating apparatus 600 determines that the user needs to be informed of the risk associated with the abnormal blood pressure, the blood pressure estimating apparatus 600 outputs an alarm sound through a speaker, or generates a vibration through a vibration generator. In another example, the blood pressure estimating apparatus 600 outputs, through the display 640, a message indicating that the current blood pressure is in an abnormal range, along with the blood pressure information estimated by the processor 620.

The blood pressure estimating apparatus 600 transmits data to an external device, for example, a mobile device, a personal computer (PC), or a network, or receives data from the external device, through the transceiver 660.

Figure 7:
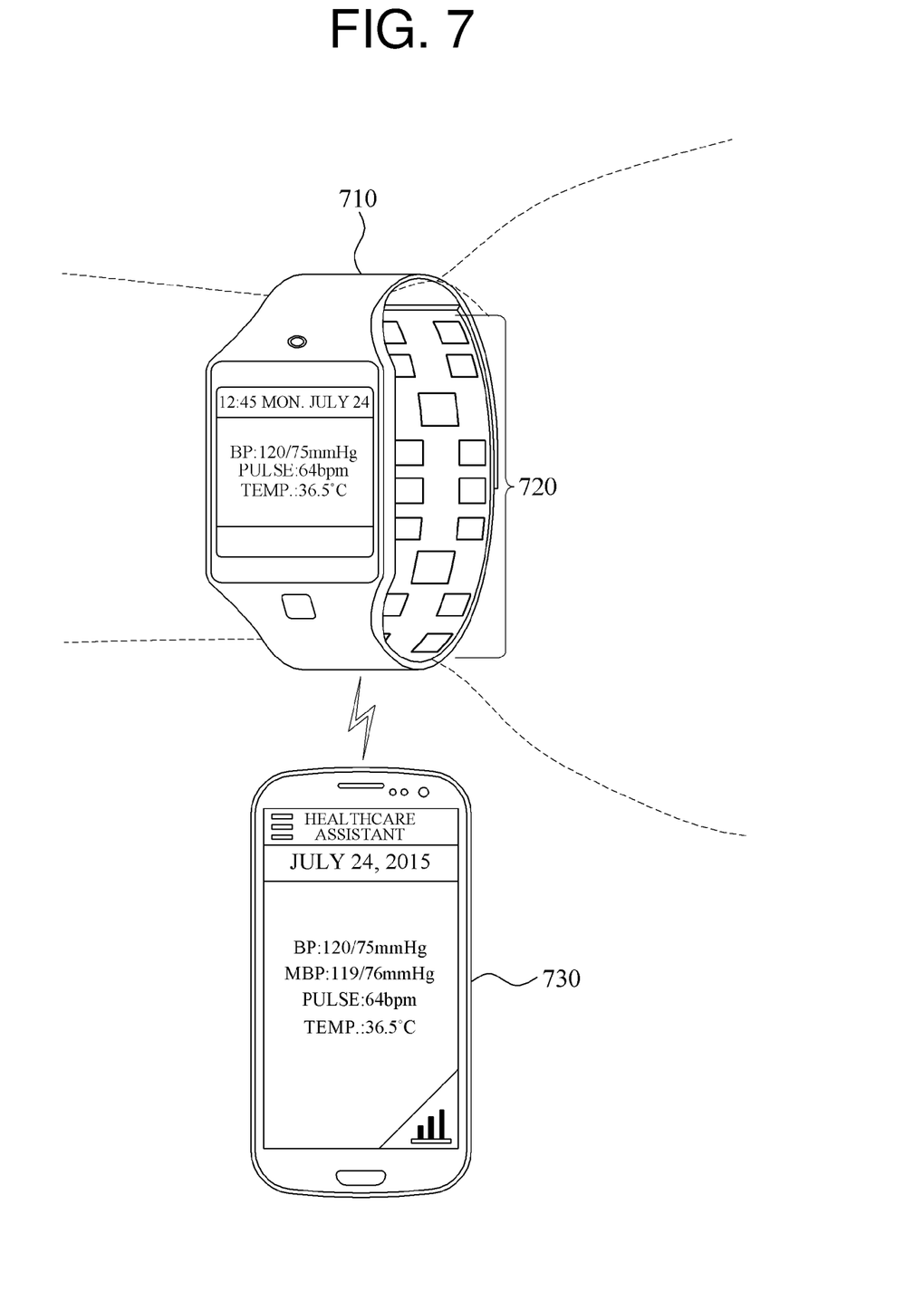
FIG. 7 illustrates an example of a blood pressure estimating apparatus applied to a wearable device.

FIG. 7 illustrates an example of a blood pressure estimating apparatus applied to a wearable device 710.

The blood pressure estimating apparatus may be configured as the wearable device 710 of a watch type as illustrated in FIG. 7. Referring to FIG. 7, a sensor unit 720 of the wearable device 710 includes sensors configured to measure a biosignal, and sensors configured to measure an auxiliary signal, for example, environment information. For example, the sensor unit 720 includes sensors configured to measure a PPG signal and an ECG signal, an acceleration sensor and a gyro sensor configured to measure movement information of a user, and a temperature sensor. The wearable device 710 conveniently measures a blood pressure of the user through the sensor unit 720 without using a cuff.

The wearable device 710 continuously measures a pulse wave signal of the user through a PPG sensor configured to sense a PPG signal. The PPG sensor includes at least one optical source configured to emit light onto a body part, and at least one optical detector configured to detect light reflected from the body part or transmitted through the body part when the light is emitted from the optical source, and convert the detected light into the PPG signal. The wearable device 710 analyzes a waveform of the PPG signal sensed by the PPG sensor, continuously estimates a blood pressure of the user using a blood pressure estimation model, and displays the estimated blood pressure.

The wearable device 710 may performs a calibration on the blood pressure estimation model to prevent a degradation of accuracy in estimating a blood pressure that may occur due to a lapse of time or a change in a situation. For example, the wearable device 710 measures an ECG signal periodically or intermittently, calculates a PTT based on the PPG signal and the ECG signal, and calibrates the blood pressure estimation model based on the calculated PTT. A portion of the sensors included in the sensor unit 720 are activated each time the calibration is performed. The wearable device 710 outputs a message requesting the user to perform an action to obtain an ECG signal.

When the wearable device 710 determines that a level of accuracy of the blood pressure estimation model has greatly decreased due to a large amount of time elapsing since a previous calibration or a rapidly changing external situation, the wearable device 710 outputs a message requesting the user to measure a blood pressure value using a cuff and input the measured blood pressure value to the wearable device 710. When the user inputs to the wearable device 710 the blood pressure value measured using the cuff, the wearable device 710 calibrates the blood pressure estimation model based on the input blood pressure value.

As described above, performing a simpler calibration method between calibrations using a cuff reduces a frequency of performing the calibration using the cuff, thus reducing an inconvenience experienced by the user when measuring a blood pressure value while wearing the cuff.

In one example, the wearable device 710 provides the user with the estimated blood pressure information of the user through a mobile device 730. The mobile device 730 analyzes the blood pressure information received from the wearable device 710, determines a health state of the user, and records a change in a blood pressure over time.

Although an example of the wearable device 710 providing the user with the blood pressure information measured by the wearable device 710 through interworking with the mobile device 730 is illustrated in FIG. 7, the blood pressure information measured by the wearable device 710 may be provided to the user through an application installed in other devices interworking with the wearable device 710, for example, a PC, a tablet PC, and a smart television (TV).

The examples described above may be implemented in various types of products, for example, a mobile device, a smart appliance, and a vehicle steering wheel, in addition to the wearable device 710 illustrated in FIG. 7.

The blood pressure estimating apparatus 100, the sensor unit 120, the signal selector 130, the calibrator 150, the blood pressure estimator 140, and the calibration controller 160 illustrated in FIG. 1 and the blood pressure estimating apparatus 600, the sensor unit 610, the processor 620, the storage 630, the display 640, the interface 650, and the transceiver 660 illustrated in FIG. 6 that perform the operations described herein with respect to FIGS. 1-7 are implemented by hardware components. Examples of hardware components include controllers, sensors, generators, drivers, memories, comparators, arithmetic logic units, adders, subtractors, multipliers, dividers, integrators, and any other electronic components known to one of ordinary skill in the art. In one example, the hardware components are implemented by computing hardware, for example, by one or more processors or computers. A processor or computer is implemented by one or more processing elements, such as an array of logic gates, a controller and an arithmetic logic unit, a digital signal processor, a microcomputer, a programmable logic controller, a field-programmable gate array, a programmable logic array, a microprocessor, or any other device or combination of devices known to one of ordinary skill in the art that is capable of responding to and executing instructions in a defined manner to achieve a desired result. In one example, a processor or computer includes, or is connected to, one or more memories storing instructions or software that are executed by the processor or computer. Hardware components implemented by a processor or computer execute instructions or software, such as an operating system (OS) and one or more software applications that run on the OS, to perform the operations described herein with respect to FIGS. 1-7. The hardware components also access, manipulate, process, create, and store data in response to execution of the instructions or software. For simplicity, the singular term "processor" or "computer" may be used in the description of the examples described herein, but in other examples multiple processors or computers are used, or a processor or computer includes multiple processing elements, or multiple types of processing elements, or both. In one example, a hardware component includes multiple processors, and in another example, a hardware component includes a processor and a controller. A hardware component has any one or more of different processing configurations, examples of which include a single processor, independent processors, parallel processors, single-instruction single-data (SISD) multiprocessing, single-instruction multiple-data (SIMD) multiprocessing, multiple-instruction single-data (MISD) multiprocessing, and multiple-instruction multiple-data (MIMD) multiprocessing.

The methods illustrated in FIGS. 4 and 5 that perform the operations described herein with respect to FIGS. 1-7 are performed by a processor or a computer as described above executing instructions or software to perform the operations described herein.

Instructions or software to control a processor or computer to implement the hardware components and perform the methods as described above are written as computer programs, code segments, instructions or any combination thereof, for individually or collectively instructing or configuring the processor or computer to operate as a machine or special-purpose computer to perform the operations performed by the hardware components and the methods as described above. In one example, the instructions or software include machine code that is directly executed by the processor or computer, such as machine code produced by a compiler. In another example, the instructions or software include higher-level code that is executed by the processor or computer using an interpreter. Programmers of ordinary skill in the art can readily write the instructions or software based on the block diagrams and the flow charts illustrated in the drawings and the corresponding descriptions in the specification, which disclose algorithms for performing the operations performed by the hardware components and the methods as described above.

The instructions or software to control a processor or computer to implement the hardware components and perform the methods as described above, and any associated data, data files, and data structures, are recorded, stored, or fixed in or on one or more non-transitory computer-readable storage media. Examples of a non-transitory computer-readable storage medium include read-only memory (ROM), random-access memory (RAM), flash memory, CD-ROMs, CD-Rs, CD+Rs, CD-RWs, CD+RWs, DVD-ROMs, DVD-Rs, DVD+Rs, DVD-RWs, DVD+RWs, DVD-RAMs, BD-ROMs, BD-Rs, BD-R LTHs, BD-REs, magnetic tapes, floppy disks, magneto-optical data storage devices, optical data storage devices, hard disks, solid-state disks, and any device known to one of ordinary skill in the art that is capable of storing the instructions or software and any associated data, data files, and data structures in a non-transitory manner and providing the instructions or software and any associated data, data files, and data structures to a processor or computer so that the processor or computer can execute the instructions. In one example, the instructions or software and any associated data, data files, and data structures are distributed over network-coupled computer systems so that the instructions and software and any associated data, data files, and data structures are stored, accessed, and executed in a distributed fashion by the processor or computer.

While this disclosure includes specific examples, it will be apparent to one of ordinary skill in the art that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner, and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

What is claimed is:

1. A blood pressure estimating apparatus, comprising:
 a first sensor configured to measure a first biosignal comprising pulse wave information of a user;
 a second sensor configured to measure a second biosignal;
 a calibration controller configured to determine a calibration time at which a calibration is to be performed on a blood pressure estimation model and a calibration method for the blood pressure estimation model, the determined calibration method being selected between a first calibration method for calibrating the blood pressure estimation model based a measured blood pressure value and a second calibration method for calibrating the blood pressure estimating model based on the second biosignal, the second calibration method taking less time than the first calibration method;
 a calibrator configured to calibrate the blood pressure estimation model at the determined calibration time using the determined calibration method; and
 a blood pressure estimator configured to estimate a blood pressure of the user from the first biosignal using the calibrated blood pressure estimation model.

2. The apparatus of claim 1, wherein the calibration controller is further configured to determine the calibration time and
 select the first calibration method for calibrating the blood pressure estimating model when the signal quality of the first biosignal is less than or equal to a threshold and/or a threshold elapsed time since a previous calibration of the blood pressure estimation model was performed has been reached; and
 select the second calibration method when the first calibration is not selected.

3. The apparatus of claim 1, wherein the calibration controller is further configured to:
 determine the calibration time and the calibration method based on any one or any combination of any two or more of movement information of the user, external temperature information, and body temperature information of the user; and
 control an operation of the first sensor.

4. The apparatus of claim 1, wherein the first calibration method of calibrating the blood pressure estimation model based on a blood pressure value measured using a cuff.

5. A blood pressure estimating apparatus, comprising:
a first sensor configured to sense a first biosignal of a user;
a blood pressure estimator configured to estimate a blood pressure of the user from the first biosignal using a blood pressure estimation model;
a calibrator configured to calibrate the blood pressure estimation model using a plurality of calibration methods;
a calibration controller configured to select one of the calibration methods, and control the calibrator to calibrate the blood pressure estimation model using the selected calibration method; and
a second sensor configured to sense a second biosignal of the user;
wherein the plurality of calibration methods comprise:
a first calibration method in which the calibrator calibrates the blood pressure estimation model based on a blood pressure of the user measured using a cuff; and
a second calibration method in which the calibrator calibrates the blood pressure estimation model based on the first biosignal and the second biosignal, and takes less time than the first calibration method.

6. The apparatus of claim 5, wherein the calibration controller is further configured to alternately select the first calibration method and the second calibration method.

7. The apparatus of claim 5, wherein the calibration controller is further configured to:
determine a signal quality of the first biosignal,
select the first calibration method in response to either the signal quality of the first biosignal being less than or equal to a predetermined threshold or a predetermined amount of time elapsing since a last calibration of the blood pressure estimation model was performed, and
select the second calibration method in response to the first calibration method not being selected.

8. The apparatus of claim 5, further comprising:
at least one additional first sensor configured to sense a first biosignal of the user so that the apparatus comprises a plurality of first sensors configured to sense a plurality of first biosignals of the user at a plurality of different sensing locations on the user; and
a signal selector configured determine respective signal qualities of the first biosignals, select one of the first biosignals having a highest signal quality, and output the selected first biosignal to the blood pressure estimator.

9. A blood pressure estimating method, comprising:
measuring a first biosignal comprising pulse wave information of a user;
measuring a second biosignal;
determining a signal quality of the first biosignal;
determining a calibration method for a blood pressure estimation model, the determined calibration method being selected between a first calibration method for calibration the blood pressure estimation model based a measured blood pressure value and a second calibration method for calibrating the blood pressure estimation model based on the second biosignal, the second calibration method taking less time than the first calibration method;
calibrating the blood pressure estimation model using the determined calibration method; and
estimating a blood pressure of the user from the first biosignal using the calibrated blood pressure estimation model.

10. The method of claim 9, wherein:
the determining of the calibration method comprises:
selecting the first calibration method for calibrating the blood pressure estimation model when the signal quality of the first biosignal is less than or equal to a threshold and/or a threshold elapsed time since a previous calibration of the blood pressure estimation model was performed has been reached; and
selecting the second calibration method when the first calibration is not selected.

11. The method of claim 9, wherein the determining of the calibration method comprises determining the calibration method for the blood pressure estimation model based on any one or any combination of any two or more of movement information of the user, external temperature information, and body temperature information of the user.

12. The method of claim 9, wherein the first calibration method of calibrating the blood pressure estimation model is based on a blood pressure value measured using a cuff.

13. The method of claim 12, wherein the determining of the calibration method comprises determining that the second calibration method is to be performed between points in time at which the first calibration method is performed.

14. The method of claim 12, wherein the first biosignal is a photoplethysmogram (PPG) signal; and the second biosignal is an electrocardiogram (ECG) signal or a biosignal comprising blood oxygen saturation ($SpO_2$) information.

15. The method of claim 9,
wherein the determining of the calibration method is performed in response to a result of determining whether to calibrate the blood pressure estimation model.

16. The method of claim 15, wherein the determining of whether to calibrate the blood pressure estimation model comprises determining whether to calibrate the blood pressure estimation model based on either one or both of a signal quality of the first biosignal and an elapsed time since a previous calibration of the blood pressure estimation model was performed.

17. The method of claim 15, wherein the determining of whether to calibrate the blood pressure estimation model comprises determining whether to calibrate the blood pressure estimation model based on any one or any combination of any two or more of movement information of the user, external temperature information, and body temperature information of the user.

18. The method of claim 9, wherein the measuring of the first biosignal comprises:
measuring first biosignals of a same type; and
selecting a reference biosignal from the first biosignals based on signal qualities of the first biosignals; and
the estimating of the blood pressure of the user comprises estimating the blood pressure of the user from the reference biosignal using the calibrated blood pressure estimation model.

19. A non-transitory computer-readable storage medium storing instructions to cause computing hardware to perform the method of claim 9.

* * * * *